United States Patent [19]

Hoskin et al.

[11] Patent Number: 5,000,752
[45] Date of Patent: Mar. 19, 1991

[54] TREATMENT APPARATUS AND METHOD

[75] Inventors: William J. Hoskin, 5 Long Buftlers, Harpenden, Hertfordshire, England, AL5 1JF; Dermot J. Pierse, London, England

[73] Assignee: William J. Hoskin, Hertfordshire, United Kingdom

[21] Appl. No.: 368,931

[22] Filed: Jun. 19, 1989

Related U.S. Application Data

[63] Continuation of Ser. No. 933,463, Nov. 20, 1986, abandoned.

[30] Foreign Application Priority Data

Dec. 13, 1985 [GB] United Kingdom ............... 8530786

[51] Int. Cl.⁵ ............................................. A61N 5/06
[52] U.S. Cl. ......................................... 606/9; 606/15; 606/16; 606/17; 128/398
[58] Field of Search ..................... 128/303.1, 395, 397, 128/398; 606/9, 13–17

[56] References Cited

U.S. PATENT DOCUMENTS

| | | | |
|---|---|---|---|
| 1,791,794 | 2/1931 | Chesney | 128/398 |
| 1,794,557 | 3/1931 | Symonds | 128/398 |
| 1,965,865 | 7/1934 | Thompson | 128/397 |
| 2,186,143 | 1/1940 | Neugass | 128/397 |
| 2,227,422 | 4/1941 | Boerstler | 128/397 |
| 3,261,928 | 7/1966 | Brenman | 128/395 |
| 3,413,067 | 11/1968 | Froio | 128/398 |
| 4,069,823 | 1/1978 | Isakov et al. | 128/303.1 |
| 4,273,127 | 6/1981 | Auth et al. | 128/303.1 |
| 4,448,198 | 5/1984 | Turner . | |
| 4,625,724 | 12/1986 | Suzuki et al. | 128/303.1 |
| 4,627,435 | 12/1986 | Hoskin | 128/303.1 |

FOREIGN PATENT DOCUMENTS

| | | | |
|---|---|---|---|
| 130950 | 1/1985 | European Pat. Off. | 128/303.1 |
| 172490 | 1/1986 | European Pat. Off. | 128/303.1 |
| 2646029 | 4/1978 | Fed. Rep. of Germany | 128/303.1 |
| 184488 | 9/1985 | Japan | 214/121 CW |
| 291865 | 6/1928 | United Kingdom . | |
| 2060397 | 5/1981 | United Kingdom | 128/303.1 |
| 8505262 | 12/1985 | World Int. Prop. O. | 128/303.1 |

OTHER PUBLICATIONS

"Blutstillung an Leber . . . ", by Lauterjung et al.; Kongress der Deutschen Gesellschaft für Chirurgie, pp. 22–25, Apr. 1981.
"Dermatologic Laser Treatment . . . ", Ohshiro; Lasers & Electro-Optik, Nov. 3, 1977, pp. 34–35.
"Fibre Bundle Scanner . . . " by Fujii et al., 1982.
"Saphir-Koagulator" by Nath, 6/20/83.

Primary Examiner—Lee S. Cohen
Assistant Examiner—David Shay
Attorney, Agent, or Firm—Christie, Parker & Hale

[57] ABSTRACT

Port wine stain treatment apparatus includes a pad supporting a plurality of diamond tipped needles. The tip of each needle is supplied with laser radiation and the tip acts to scatter laser radiation sideways. Thus, when the pad is applied to the skin, the tips penetrate the skin and when laser radiation is supplied the tips create a laminar radiation profile located below and spaced from the skin surface. In this manner, the cause of the port wine stain can be treated without the danger of disfiguring or scarring the skin surface above the stain.

7 Claims, 3 Drawing Sheets

TREATMENT APPARATUS AND METHOD

CROSS-REFERENCE TO RELATED APPLICATIONS

This is a continuation of application Ser. No. 06/933,463, filed Nov. 20, 1986, now abandoned.

BACKGROUND OF THE INVENTION

1. Field of the Invention

The present invention relates to apparatus for and a method of treating conditions, for example the medical phenomenon known colloquially as port wine stains.

2. Description of the Prior Art

Port wine stains are manifest by deep red discolourations of the skin often on the face which are embarrassing and disfiguring to the bearer. Port wine stains are believed to emanate from enlarged or burst blood vessels located some 0.5 to 1.5 mm below the surface of the skin.

Current treatment involves shrinking or sealing the blood vessels by the application of laser radiation through the skin. The process is very slow because the laser is a point source and hazardous because insufficient radiation will not have the desired effect and too much radiation will cause scarring of the skin surface.

It is an object of the invention to provide an improved apparatus and method for curing conditions such as port wine stains.

SUMMARY OF THE INVENTION

According to the present invention there is provided treatment apparatus comprising a support member, having an abutment surface arranged to bear against a member to be treated, an array of elongate elements supported by the member and extending generally parallel to said abutment surface, each elongate member supporting a radiation dispersing tip in spaced relationship with the abutment surface, and means communicating radiation axially of each elongate member to a corresponding said tip for dispersal from said tip in directions generally parallel to said abutment surface to define a generally laminar radiation pattern in planes spaced from but extending parallel to said abutment surface.

According to the present invention there is further provided apparatus for treating port wine stains comprising a flexible pad supporting a plurality of skin penetration elements projecting from an abutment surface thereof, a source of laser radiation, means coupling the source to each element, and a plurality of laser beam dispersing tips, one tip located on the free end of each element, the tips being arranged to disperse laser radiation in a direction generally parallel to said abutment surface, whereby to create a generally laminar radiation pattern below and spaced from the surface of the skin when the pad is applied to the skin in a manner to cause the said tips to puncture and penetrate below the surface of the skin.

According to the present invention there is still further provided a method of treating port wine stains comprising, in an area of port wine stains, creating a laminar laser radiation pattern located below and spaced from the surface of the skin and sustaining said pattern for a period sufficient to constrict the blood vessels in that area to remove the cause of said stains.

According to the present invention there is still further provided a surgical needle comprising an elongate shaft, a diamond tip mounted at the free end of the shaft, a laser, a fibre optical conductor extending inside the shaft to optically couple the laser to the diamond tip, the diamond tip being cut to have a planar face extending parallel to the axis of the shaft and through which substantially no laser energy will propagate and otherwise profiled to distribute laser energy in a generally laminar pattern extending generally parallel to the face.

BRIEF DESCRIPTION OF THE DRAWINGS

Apparatus for and a method of treating port wine stains and embodying the present invention will now be described, by way of example, with reference to the accompanying diagrammatic drawings, in which.

DESCRIPTION OF THE PREFERRED EMBODIMENTS

Figure 1:
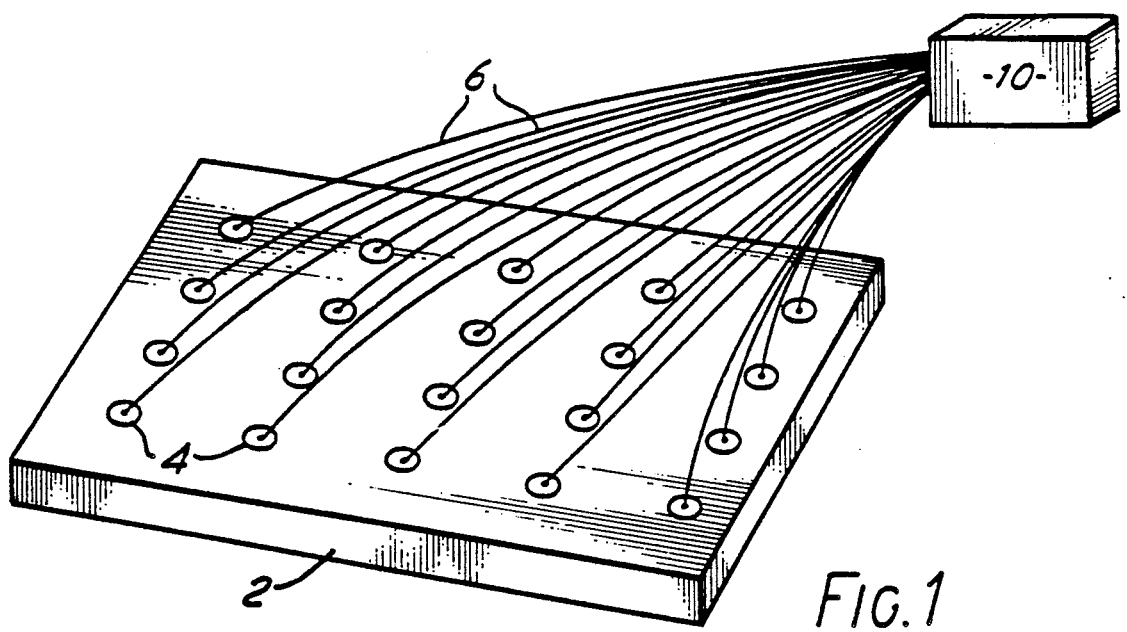
FIG. 1 is a perspective view of the apparatus for treating port wine stains.
Figure 2:
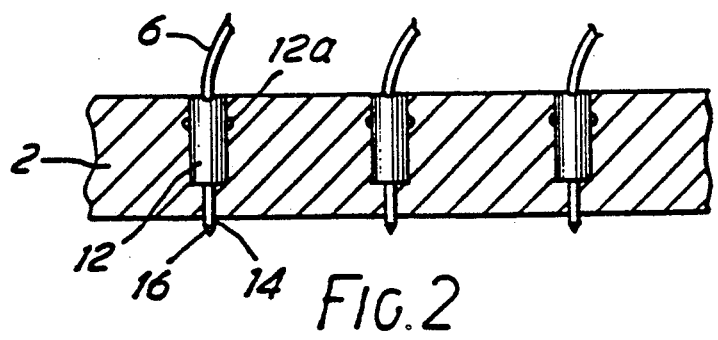
FIG. 2 is a fragmentary section through the apparatus of FIG. 1.

As shown in FIG. 1, the apparatus comprises a flexible or malleable pad or strip 2 of plastics material supporting an array of needle assemblies 4. Each needle assembly is coupled by an optical fibre 6 to a laser assembly 10.

The laser assembly 10 is arranged to supply each optical fibre with laser energy either simultaneously or in rotation.

Each needle assembly 4 comprises a support body 12 held captive in the strip 2, a needle element 14 which is screwthreadedly engaged with the support body 12 and a diamond or sapphire tip 16 of conical configuration. The support body 12, while held captive in the strip 2 due to the presence of an annular flange 12a, can rotate and if rotated will draw up or let down the needle element 14 so as to allow the distance of the tip 16 from the underside of the strip 2 to be adjusted. Instead, the needle element 14 can be displaced by a cam mechanism for example.

Each needle element 14 comprises a hollow tube 20 which accommodates the end portion of the fibre 6. The butt end of the tip is optically polished and is optically coupled to the fibre 6. The tip 16 can be swaged, glued or brazed to the hollow tube 20.

The tip 16 is advantageously in the form of a diamond cone having a maximum diameter in the range of from 0.25 to 1 mm. The cone angle is advantageously 45° so as to provide a substantially disc-shaped radiation pattern. For different materials having a different refractive index, a different cone angle will be required to provide the desired radiation profile.

The needle elements 14 are preferably adjustable such that the distance of the point on the tip 16 from the underside of the strip 2 can be varied over the range of from 0.20 mm to 2.50 mm.

In operation the needles element 14 are adjusted to provide a particular depth of penetration for a particular patient.

Figure 5:
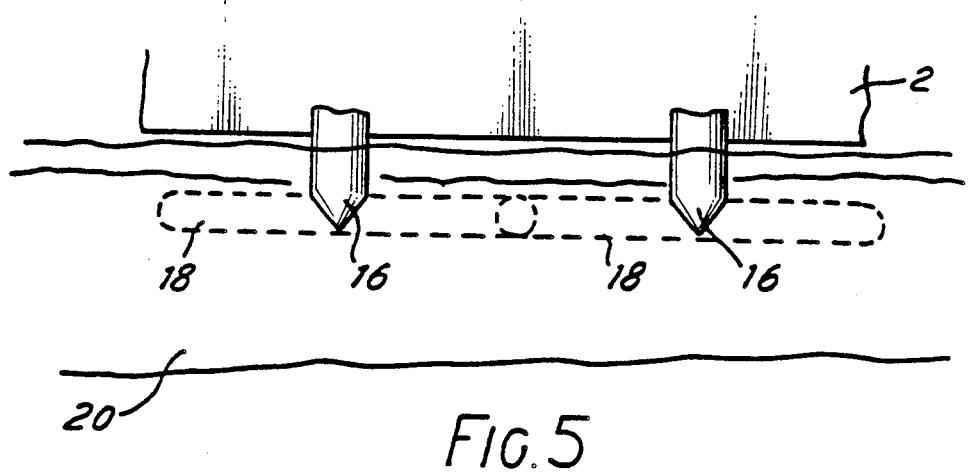
FIG. 5 is a fragmentary view of the apparatus acting on the skin of a patient.

The patient is given a general anaesthetic (in some cases a local anaesthetic will suffice) and the strip 2 is pressed down upon the area requiring treatment to cause the tips 16 to penetrate the upper layer of the skin to the required depth. If the strip 2 is transparent, the proper positioning of the tips can be visually checked. The laser assembly 10 is energised to provide each fibre with 0.5 watts of laser radiation for a period generally of 5 seconds. The tips 16 would then generate overlapping radiation patterns 18 (see FIG. 5) to treat the area causing the port wine stain. This level of energy is considered sufficient to constrict blood vessels over a radius of 2.5 to 3.0 mm. The strip 2 is then removed and in due course the port wine stain should clear.

As hereinbefore indicated, the fibres 6 could be supplied with laser radiation either simultaneously or in rotation. If supplied in rotation, the laser assembly need only have a single relatively low powered laser. For example, a Neodymium YAG Laser having a variable power output from 100 mW to 3 watts could be used. The supplied power could be continuous or pulsed.

Instead of treating the port wine stain in a single application of the strip 2, the treatment could be effected by two or more applications of the strip 2. Thus, for example, by doubling the spacing between the needles, a pattern of selected areas would be treated on a first application of the strip and a pattern of the areas intervening the selected areas could be treated on a second application of the strip.

Where port wine stains having an irregular shape are to be treated, the area in question may be treated by the application of a plurality of smaller strips 2 mosaiced to provide blanket coverage of the area.

Figure 3:
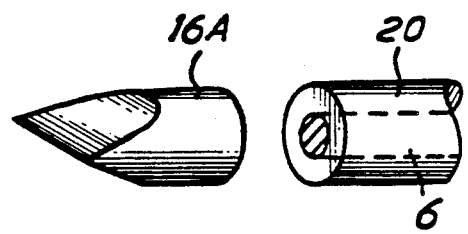
FIGS. 3 and 4 are fragmentary exploded views of two modified needles for the apparatus of FIG. 1.
Figure 4:
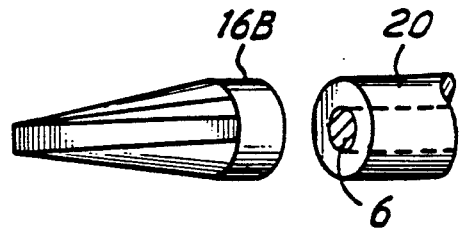

In a modification, the tip 16 can be replaced by the modified tip 16A or 16B as shown in FIGS. 3 and 4.

It will be appreciated that the apparatus may also be used for effecting treatment of conditions other than port wine stains, for example in the removal of tattoo marks.

Figure 6:
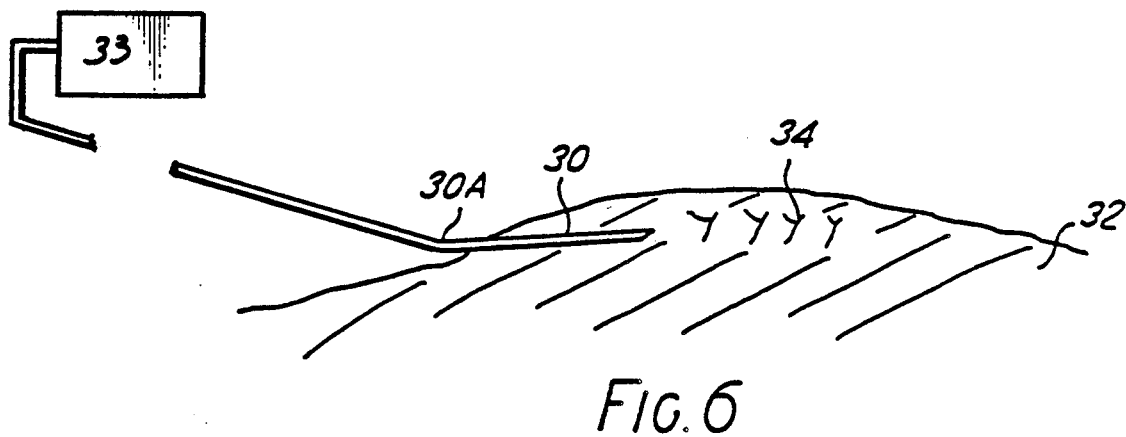
FIG. 6 is a section through a patient's skin showing a modified needle inserted therein.

FIG. 6 shows a modified form of needle. As shown, the needle 30 has an elbow portion 30A defining an angle in the range of between 180° to 90° to allow the free end of the needle to be inserted below the surface of a patient's skin 32 in a direction parallel to the skin surface to direct laser radiation from a laser source 33 towards enlarged blood vessels 34.

Figures 7, 7A:
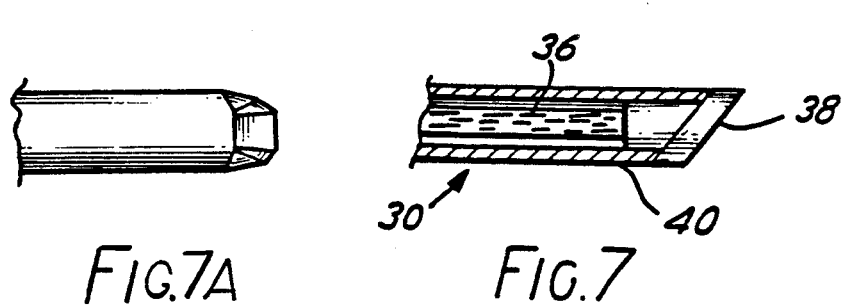
FIG. 7 is a fragmentary section to an enlarged scale of the needle of FIG. 6.
FIG. 7A is an under plan of the needle of FIG. 6.

The tip of the needle 30 is shown more clearly in FIGS. 7 and 7A. As shown, the tip comprises a diamond 38 supported at the free end of a hollow tube 40. An optical fibre 36 within the tube 40 is coupled to the diamond tip.

The free end of the tube 40 defines an opening which is inclined to a plane perpendicular to the axis of the tube. In this way part of the free end of the tube acts as a lateral shield for the diamond tip to direct radiation generally only in the downward direction (as shown in FIGS. 6, 7 and 7A).

By this means the surface of the skin is shielded from the radiation produced.

The needle shown in FIGS. 6, 7 and 7A may be used singly or a plurality of such needles may be mounted on a support to provide an array of needles.

In operation the needle or needles are pushed under the skin and displaced progressively in a direction parallel to the skin. The effect is to subject the area under the skin (i.e. the area of the port wine stain) to a generally laminar radiation pattern which lies spaced from but generally parallel to the surface of the skin.

Figure 8:
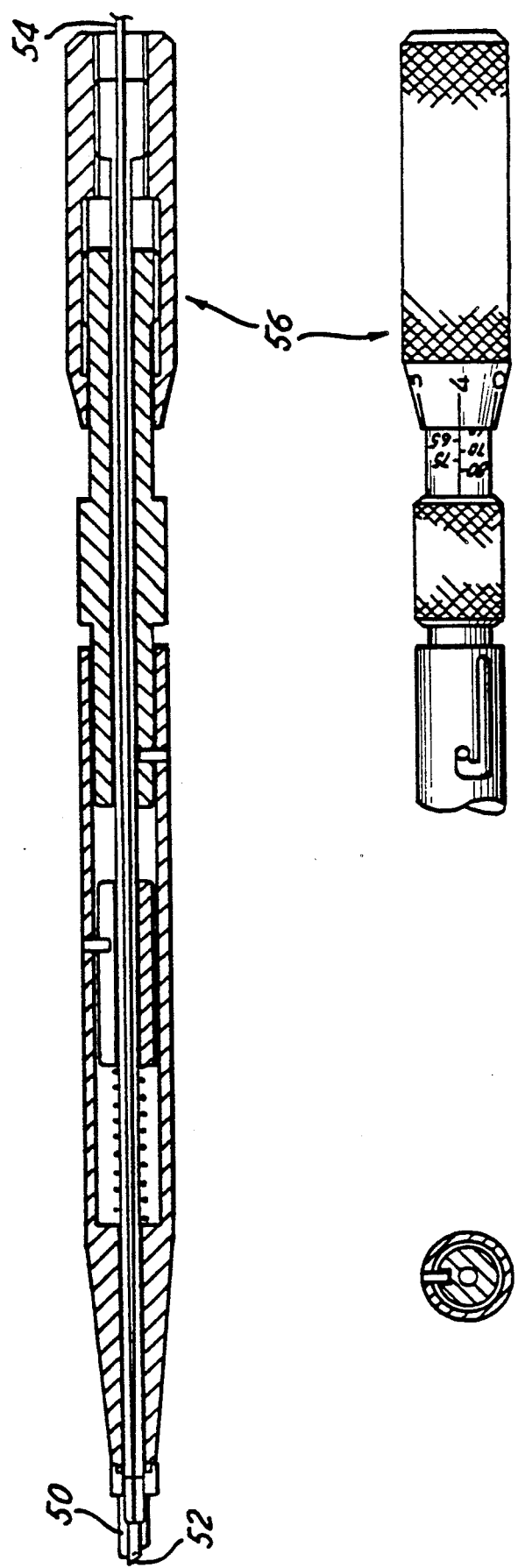
FIG. 8 is a longitudinal section through a radial keratotomy knife for introducing laser radiation below the skin surface.

The removal of port wine stains may also be performed with the aid of a radial keratotomy knife as shown in FIG. 8. As shown, the knife includes a depth guard 50 surrounding a blade or needle 52. The depth guard 50 may be adjusted by means of a vernier scale adjustment mechanism 56. An optical fibre 54 extends through the body of the knife.

It will be appreciated that a plurality of such knives can be mounted on a single block to define an array of needles similar to that shown in FIG. 1.

While a presently preferred embodiment of the present invention has been illustrated and described, modifications and variations thereof will be apparent to those skilled in the art given the teachings herein, and it is intended that all such modifications and variations be encompassed within the scope of the appended claims.

We claim:

1. An array of surgical needles for insertion into living tissue for use in treating port wine stains comprised of blood vessels in an area beneath the skin of a patient under treatment, each surgical needle comprising:
   an elongate shaft having a free end,
   a radiation disbursing tip mounted on the free end of the shaft and adapted to penetrate the skin, and
   means communicating radiation from a radiation source axially of each elongate shaft to the needle tip; and
   means supporting the array of needles in a position to penetrate the skin, and in which the needles are profiled and held spaced apart on the supporting means so that the radiation dispersed by one tip overlaps the radiation disbursed by an adjacent tip to thereby disperse the radiation in a generally laminar pattern extending generally parallel to and below the tissue surface and substantially at right angles to the axis of the needles, said laminar radiation pattern being sustainable sufficiently to constrict blood vessels in an area below the skin at which the laminar radiation pattern is dispersed for treating the port wine stains.

2. Apparatus, according to claim 1, including means for adjusting the distance between the tip of each needle and the supporting means.

3. Apparatus for treating port wine stains comprised of blood vessels in an area beneath the skin of a patient under treatment, the apparatus comprising:
   a flexible pad having an abutment surface,
   a plurality of skin penetration elements having free ends carried by the pad and projecting from said abutment surface,
   a source of laser radiation,
   means coupling the laser radiation source to each skin penetration element, and
   a plurality of laser beam dispersing tips, one tip located on the free end of each skin penetration element for dispersing said radiation from the tips of the elements, the skin penetration elements being profiled and being held spaced apart from one another by the flexible pad in a pattern thereon such that the radiation generated from the radiation source and produced by each tip overlaps the radiation produced by an adjacent tip to disperse laser radiation in a pattern extending generally parallel to said abutment surface and thereby create a generally laminar radiation pattern below and spaced from the surface of the skin and extending generally at a right angle to the axis of the skin penetration elements, when the pad is applied to the skin in a manner to cause said tips to puncture and penetrate below the surface of the skin, said laminar radiation pattern being sustainable to sufficiently constrict blood vessels in an area below the skin at which the laminar radiation pattern is dispersed for treating the port wine stains.

4. Apparatus according to claim 3, wherein the pad is of flexible transparent plastics material.

5. Apparatus according to claim 3, wherein each skin penetration element and associated tip comprises a diamond tipped hollow needle.

6. Treatment apparatus according to claim 5 wherein:
the pad supports a plurality of needles arranged in an array to distribute laser energy over an enlarged generally laminar pattern.

7. Apparatus according to claim 3 including means for adjusting the distance between the tip of each element and the abutment surface of the flexible pad.

* * * * *